United States Patent [19]

Briody et al.

[11] Patent Number: 5,739,365

[45] Date of Patent: Apr. 14, 1998

[54] METHOD FOR PREPARING AMMONIUM HYDROXYALKYL SULFONATES AND AMMONIUM ALKANOYL ALKYL SULFONATES PRODUCED THEREFROM

[75] Inventors: Robert G. Briody, Apollo, Pa.; Amy E. Doty, Crystal Lake, Ill.; Cheruthur Govindan, Murrysville; Louis J. Nehmsmann, Apollo, both of Pa.; Alan E. Wang, Hoffman Estates, Ill.

[73] Assignee: PPG Industries, Inc., Pittsburgh, Pa.

[21] Appl. No.: 509,018

[22] Filed: Jul. 28, 1995

Related U.S. Application Data

[63] Continuation of Ser. No. 289,456, Aug. 12, 1994, abandoned, which is a continuation of Ser. No. 85,062, Jun. 29, 1993, abandoned, which is a continuation-in-part of Ser. No. 721,741, Jun. 26, 1991, abandoned.

[51] Int. Cl.$^6$ .................................................. C07C 53/00
[52] U.S. Cl. ................................................ 554/92; 562/112
[58] Field of Search .................................. 554/92; 562/112

[56] References Cited

U.S. PATENT DOCUMENTS

| | | |
|---|---|---|
| 2,820,818 | 1/1958 | Sexton et al. . |
| 3,321,498 | 5/1967 | Kortland et al. ............. 562/112 |
| 3,383,396 | 5/1968 | Cahn et al. . |
| 3,420,858 | 1/1969 | McCrimist et al. ............. 554/92 |
| 3,424,770 | 1/1969 | Stein et al. ............. 562/112 |
| 3,429,136 | 2/1969 | Holt et al. . |
| 3,686,239 | 8/1972 | Passal et al. ............. 560/222 |
| 3,838,084 | 9/1974 | Hutson et al. . |
| 3,880,897 | 4/1975 | Landy ............. 554/92 |
| 4,405,526 | 9/1983 | Lamberti et al. . |
| 4,435,328 | 3/1984 | Lamberti et al. ............. 562/112 |
| 4,499,028 | 2/1985 | Longley ............. 554/92 |
| 4,515,721 | 5/1985 | Login et al. . |
| 4,536,338 | 8/1985 | Urban et al. ............. 554/92 |
| 4,612,136 | 9/1986 | Novakovic et al. . |
| 4,663,070 | 5/1987 | Dobrovolny et al. . |
| 4,696,773 | 9/1987 | Lukenbach et al. . |
| 4,790,956 | 12/1988 | Weipert et al. ............. 252/538 |
| 4,910,330 | 3/1990 | McGee et al. ............. 560/222 |

FOREIGN PATENT DOCUMENTS

| | | |
|---|---|---|
| 687540 | 5/1964 | Canada . |
| 869744 | 6/1961 | United Kingdom ............. 554/92 |
| 917952 | 2/1963 | United Kingdom . |

OTHER PUBLICATIONS

"Role of Detergents in Shampoos", by Donald H. Powers et al., Journal of the Society of Cosmetic Chemistry, vol. 10, pp. 116–122 (1959).

*Primary Examiner*—Keith MacMillan
*Attorney, Agent, or Firm*—Irwin M. Stein

[57] ABSTRACT

A method is disclosed for preparing ammonium hydroxyalkyl sulfonate by a process of reacting ammonium bisulfite and alkylene oxide wherein the pH is maintained at a relatively low value throughout most of the time of reaction of ammonium bisulfite and alkylene oxide in order to minimize the quantity of impurities, e.g. alkylene glycol and alkanolamine, in the ammonium hydroxyalkyl sulfonate. Ammonium alkanoyl alkyl sulfonates prepared by reacting such ammonium hydroxyalkyl sulfonates with fatty acids form aqueous solutions which are clear at ambient temperatures, and thus are useful as surfactants in clear liquid products.

20 Claims, No Drawings

METHOD FOR PREPARING AMMONIUM HYDROXYALKYL SULFONATES AND AMMONIUM ALKANOYL ALKYL SULFONATES PRODUCED THEREFROM

CROSS REFERENCE TO RELATED APPLICATION

This is a continuation of application Ser. No. 08/085,062, filed Jun. 29, 1993, now abandoned, which is a continuation-in-part of U.S. Application Ser. No. 07/721,741 filed Jun. 26, 1992, now abandoned by C. Govindan, commonly assigned.

BACKGROUND

The present invention relates to the preparation of ammonium hydroxyalkyl sulfonates, e.g. ammonium isethionate, which are particularly useful in the production of ammonium alkanoyl alkyl sulfonate surface-active materials, and more particularly relates to the preparation of ammonium salts of fatty acid esters of hydroxyalkyl sulfonic acids. Still more particularly, the present invention relates to a process for utilizing ammonium isethionate in solution for preparing surface-active materials of the general formula RCO(O)R'SO$_3$M, wherein R is a monovalent aliphatic hydrocarbon radical having from 5 to 23 carbon atoms, R' is a bivalent alkylene radical containing from 2 to 4 carbon atoms and M is the ammonium cation. In a preferred embodiment, the present invention relates to the use of ammonium isethionate in aqueous solution for the preparation of ammonium salts of alkanoyl isethionate, e.g. ammonium cocoyl isethionate.

Alkali metal, i.e. sodium or potassium, salts of alkanoyl alkyl sulfonates are described in U.S. Pat. No. 3,429,136. Of such materials, sodium cocoyl isethionate is the most widely used commercially in personal care applications, e.g. in synthetic detergent bars, as described in U.S. Pat. No. 4,663,070. Sodium cocoyl isethionate (SCI) is practically insoluble in water at room temperature, and hence its use in clear liquid formulations such as shampoos is limited.

In contrast, copending U.S. Ser. No. 07/721,741 discloses that the ammonium salt of cocoyl isethionic acid, i.e. ammonium cocoyl isethionate (ACI), is very soluble in water at room temperature. Because of its high solubility in water, it has been found that clear, i.e. non-turbid, solutions of up to about 40 weight percent of relatively pure ACI, i.e. ACI of at least 85 percent anionic activity, may be prepared. At present, there are no known commercial sources for ammonium alkanoyl alkyl sulfonates, e.g. ammonium cocoyl isethionate. While U.S. Pat. No. 4,663,070 refers generally to ammonium salts of C$_{10}$ to C$_{16}$ acyl isethionate, a process for preparing such materials, particularly of high purity and anionic activity, has not been described, particularly with respect to ammonium isethionate in aqueous solution.

U.S. Ser. No. 07/721,741, the full disclosure of which is incorporated herein by reference, discloses that ammonium alkanoyl alkyl sulfonates, e.g. ammonium alkanoyl isethionate such as ammonium cocoyl isethionate, may be prepared by heating an ammonium hydroxyalkyl sulfonate, e.g. ammonium isethionate, with a fatty acid having from about 6 to about 24 carbon atoms at temperatures below which charting of the ammonium alkanoyl alkyl sulfonate product occurs. It is further disclosed that the aforedescribed solid product may be removed from the reaction vessel as an aqueous solution without serious decomposition due to hydrolysis by mixing a small amount of an alkaline reagent, preferably a high boiling, relatively non-volatile, relatively water-free organic sine, e.g. a tertiary amine such as triethanolamine, with the product to adjust its acidity to a near neutral pH of from about 6 to about 8, and subsequently dissolving the product in water, thereby to form an aqueous solution of the ammonium alkanoyl alkyl sulfonate. Substantially clear, i.e. non-turbid, solutions of such a product may be used in cosmetic applications such as clear shampoo formulations.

SUMMARY OF THE INVENTION

The present invention involves ammonium alkanoyl alkyl sulfonates, e.g. ammonium cocoyl isethionate, prepared from a fatty acid, e.g. coco fatty acid, and an ammonium hydroxyalkyl sulfonate, e.g. ammonium isethionate, wherein the ammonium hydroxyalkyl sulfonate, e.g. ammonium isethionate, is prepared by reacting ammonium bisulfite with an alkylene oxide, e.g. ethylene oxides under controlled pH conditions. The method of the invention yields substantially pure ammonium hydroxyalkyl sulfonate, e.g. ammonium isethionate, having low levels of impurities such as ammonium sulfate, alkanolamine, e.g. ethanolamine, and alkylene glycol, e.g. ethylene glycol. As a result of this method of preparing the ammonium hydroxyalkyl sulfonate, e.g. ammonium isethionate, the ammonium hydroxyalkyl sulfonate may be used directly as an aqueous solution to react with a fatty acid, e.g. coco fatty acid, to form ammonium alkanoyl alkyl sulfonate, e.g. ammonium cocoyl isethionate, without having to crystallize the ammonium hydroxyalkyl sulfonate, e.g. ammonium isethionate, in order to reduce impurities to levels sufficiently low that the resulting ammonium alkanoyl alkyl sulfonate, e.g. ammonium cocoyl isethionate, has an acceptably low color and clear point to be used in clear liquid products. Two methods of controlling the pH during the reaction of ammonium bisulfite and alkylene oxide, e.g. ethylene oxide, are described in detail hereafter. One method involves lowering the initial pH of the reaction mixture of ammonium bisulfite and alkylene oxide, e.g. ethylene oxide. Another method involves adding an acidic neutralizing agent in response to increasing pH to maintain the pH within a prescribed range substantially throughout the reaction.

DETAILED DESCRIPTION OF THE INVENTION

Surface-active materials of the general formula RCO(O)R'SO$_3$M wherein M is ammonium cation, i.e. ammonium alkanoyl alkyl sulfonates, may be prepared by a process involving the direct esterification of a fatty acid with an ammonium hydroxyalkyl sulfonate, particularly ammonium isethionate in aqueous solution. In the preceding general formula, R represents the aliphatic hydrocarbon residue of a fatty acid containing from 6 to 24 carbon atoms, i.e. R is a monovalent aliphatic hydrocarbon radical containing from 5 to 23 carbon atoms, and R' represents a bivalent hydrocarbon radical containing from 2 to 4 carbon atoms. Preferably, R is an aliphatic hydrocarbon radical having from about 7 to about 17 carbon atoms for reasons of solubility and detergency. More preferably, R is an aliphatic hydrocarbon radical containing from about 9 to about 17 carbon atoms, and R' is the bivalent ethylene radical, i.e. (—CH$_2$—CH$_2$—).

The aliphatic hydrocarbon radical R includes linear and branched aliphatic radicals, and further includes mixtures of aliphatic radicals within the described carbon chain length, as are found, for example, in fatty acids derived from natural fats or oils. Fatty acids used in the present process may be prepared synthetically, but are conveniently available as the mixed fatty acids derived from naturally occurring vegetable fats and oils, such as coconut oil, palm oil, babassu oil, castor oil, olive oil, peanut oil, rape seed oil, corn oil, sesame seed oil, cotton seed oil, soybean oil, sunflower seed oil, safflower seed oil and hemp oil (hydrogenated and unhydrogenated). Lauric, caprylic, caproic, myristic, palmitic, stearic, palmitoleic and oleic acids also can be used, alone or in admixture, or in substitution for a part of the fatty acid reactant. Fatty acids derived from coconut oil, which comprise a mixture of principally $C_8$ to $C_{18}$ fatty acids, represent the preferred fatty acid reactant.

The ammonium salt of the hydroxyalkyl sulfonic acid used as a reactant in the process described herein may be represented by the general formula HOR' $SO_3M$ wherein R' and M are the same as defined hereinabove. More particularly, the ammonium hydroxyalkyl sulfonate reactant may be represented by the general formula

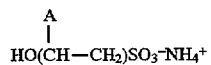

$$\text{HO(CH—CH}_2\text{)SO}_3^-\text{NH}_4^+$$
$$|$$
$$\text{A}$$

wherein A is selected from the group consisting of hydrogen, methyl and ethyl, preferably hydrogen, i.e. ammonium isethionate.

Copending U.S. Ser. No. 07/721,741 discloses that ammonium hydroxyalkyl sulfonate used in the above-described esterification process may be prepared by the reaction of ammonium bisulfite with an alkylene oxide containing from 2 to 4 carbon atoms, i.e. ethylene oxide, propylene oxide or burylone oxide, as described, for example, in U.S. Pat. 2,820,818, and reports that commercially available ammonium bisulfite has been found to contain significant amounts of ammonium sulfate as an impurity, e.g. 2 percent ammonium sulfate in a 60 percent ammonium bisulfite solution. Ammonium sulfate present in the ammonium bisulfite reactant is also then present as an impurity in the ammonium hydroxyalkyl sulfonate prepared from such ammonium bisulfite. For example, ammonium isethionate prepared from commercially available ammonium bisulfite has been found to contain as much 6.5 weight percent ammonium sulfate.

Copending U.S. Ser. No. 07/721,741 further discloses that ammonium hydroxyalkyl sulfonate, e.g. ammonium isethionate, preferably containing less than two weight percent ammonium sulfate, may be obtained by reacting pure sulfur dioxide with ammonia followed by reacting the resulting ammonium bisulfite with a $C_2$ to $C_4$ alkylene oxide, e.g. ethylene oxide. It further discloses that ammonium hydroxyalkyl sulfonate, e.g. ammonium isethionate, containing less than 2, preferably less than 1, weight percent of ammonium sulfate may be prepared by purifying commercially available ammonium bisulfite, or by purifying the ammonium hydroxyalkyl sulfonate prepared therefrom, for example by crystallizing ammonium isethionate. Such crystallized ammonium isethionate typically can be obtained with less than one weight percent ammonium sulfate.

The present invention provides a method for producing ammonium hydroxyalkyl sulfonates, e.g. ammonium isethionate, which ammonium hydroxyalkyl sulfonates, as produced from commercially available ammonium bisulfite, have sufficiently low levels of impurities that they can be used, without crystallization, to produce ammonium alkanoyl alkyl sulfonates, e.g. ammonium cocoyl isethionate, which are sufficiently clear, especially at ambient temperatures, so as to be usable in clear liquid products, and which can be produced in a commercially practicable reaction time. The method of producing such relatively pure ammonium hydroxyalkyl sulfonates, e.g. ammonium isethionate, requires controlling the pH of the reaction mixture of ammonium bisulfite and alkylene oxide, e.g. ethylene oxide. The pH of such a reaction mixture naturally rises as the reaction proceeds. In accordance with the present invention, there are disclosed two preferred embodiments for controlling the pH, preferably in the range of about 4.3 to 7.0.

In one preferred embodiment of the present invention, the initial pH of the reaction mixture of ammonium bisulfite and alkylene oxide, e.g. ethylene oxide, is brought into the range of 4.5 to 5.2, preferably 4.6 to 5.0, most preferably about 4.7. Lowering the initial pH to the aforedescribed range reduces the proportion of ammonium ion available to react with alkylene oxide to produce alkanolamines. The pH of the reaction mixture will still increase as the reaction proceeds, but it will remain closer to neutral substantially throughout the reaction. Preferably, the pH will be maintained below about 7 until the reaction is at least 90 percent, preferably closer to 95 percent, complete as measured by the amount of residual sulfite.

In another preferred embodiment of the present invention, the pH of the reaction mixture of ammonium bisulfite and alkylene oxide, e.g. ethylene oxide, which is typically about 5.5 to 6.0, is maintained in the range of about 5.5 to 7.0 substantially throughout the reaction, whereas the pH would otherwise increase, by addition of an acidic neutralizing agent as required in amounts sufficient to maintain the pH in the desired range substantially throughout the reaction cycle. The neutralizing agent may be an acid such as sulfurous acid, but is preferably sulfur dioxide, $SO_2$, which may be expeditiously added by bubbling $SO_2$ gas into the reaction mixture.

For example, ammonium bisulfite solution is reacted with an equimolar amount of ethylene oxide; samples of the reaction mixture are taken periodically, analyzed for sulfite content and pH. When the pH of the reaction mixture rises to a level near or above 7, $SO_2$ is added, continuously or intermittently, to keep the pH between about 6 and 7. Additional ethylene oxide is added to the reaction mixture in amounts that are stoichiometrically equivalent to the added $SO_2$. The reaction mixture is analyzed again for pH and sulfite content. Additional ethylene oxide is added, equivalent to the residual amount of sulfite, and this sequence is repeated until the residual sulfite level is acceptable, generally less than 0.35 weight percent, and preferably less than 0.2 weight percent. The reaction mixture is then vacuum stripped to remove any residual ethylene oxide, and the resulting ammonium isethionate can be reacted with coco fatty acid to make ammonium cocoyl isethionate.

When ammonium bisulfite is reacted with alkylene oxide, e.g. ethylene oxide, to produce the corresponding ammonium hydroxyalkyl sulfonate product, e.g. ammonium isethionate, the corresponding alkanolmnines and alkylene glycol, such as ethanolamines and ethylene glycol, are formed by the reaction of the alkylene oxide with ammonia or water, respectively, and are present as impurities in the product. For example, amounts from 1 to about 4 weight percent of ethylene glycol and up to 12 weight percent ethanolamines have been found in ammonium isethionate prepared by reacting ethylene oxide with typical commercially available ammonium bisulfite.

In either of the above described embodiments, it is preferred to maintain the solids concentration of the reaction mixture of ammonium bisulfite and alkylene oxide, e.g. ethylene oxide, at less than 70 weight percent to maintain low levels of alkylene glycol in the ammonium hydroxyalkyl sulfonate product. Alkylene glycol, e.g. ethylene glycol, which is typically present as an impurity in such ammnonium hydroxyalkyl sulfonate in amounts of from two to four weight percent, may be removed by vacuum stripping of the product. Vacuum stripping of the ammonium hydroxyalkyl sulfonate, e.g. ammonium isethionate, to remove alkylene glycol impurity will readily reduce the alkylene glycol level to less than 1 weight percent, e.g. less than 0.5 weight percent. For example, temperatures of about 140° C. pressures of about four to five millimeters (mm) of mercury (Hg) are adequate to reduce the ethylene glycol level of ammonium isethionate to less than 0.5 weight percent. Low levels of alkylene glycol are maintained to minimize the reaction of alkylene glycol with fatty acid to form alkylene glycol esters which are relatively insoluble in water, and which therefore cloud solutions of the ammonium alkanoyl alkyl sulfonate product.

The presence of significant amounts of ammonium sulfate, alkanolamine and/or alkylene glycol impurities in the ammonium hydroxyalkyl sulfonate have been found to delay the onset of the reaction of fatty acid with the ammonium hydroxyalkyl sulfonate, thereby resulting in increased reaction times. Products of lower purity and anionic activity, e.g. less than 85 percent anionic activity, are also produced when such impurities are present. Such products have poor color and yield turbid aqueous solutions. For example, it has been observed that the reaction of coco fatty acid with an ammonium isethionate aqueous solution obtained by ethoxylation of commercially available ammonium bisulfite required 14 to 16 hours at 180° C. to complete. The ammonium cocoyl isethionate product thus obtained was very dark, had a slight sulfide odor and gave dark turbid aqueous solutions. Further, the anionic activity of the product thus obtained was only in the range of 80 to 82 percent. The addition of conventional catalysts such as dodecylbenzenesulfonic acid, zinc oxide and quaternary ammonium compounds to the aforedescribed reaction was found to have no significant effect on reducing reaction times when significant amounts of ammonium sulfate and alkylene glycol impurities are present in the ammonium hydroxyalkyl sulfonate reactant.

In contrast, the reaction between coco fatty acid and an ammonium hydroxyalkyl sulfonate, e.g. ammonium isethlonate, produced in accordance with the present invention, which is thus devoid of significant amounts of impurities, i.e. having less than about one weight percent of alkylene glycol, two weight percent a alkanolamine and two weight percent ammonium sulfate, has been found to proceed readily at 180° C. The reaction begins in one to two hours. Subsequently, the reaction mixture becomes homogeneous, and water begins to distill. The reaction is completed in a total of about six to ten hours to produce good yields, e.g. 90 to 00 percent, of ammonium cocoyl isethionate having high purity, e.g. 90 to 97 percent. Aqueous solutions prepared from such a product are substantially clear, i.e. non-turbid.

In accordance with a preferred embodiment of the present invention, ammonium alkanoyl alkyl sulfonate, e.g. ammonium cocoyl isethionate, having an anionic activity of greater than 85 percent, e.g. 86 to 97 percent, is prepared by heating ammonium hydroxyalkyl sulfonate, e.g. ammonium isethionate, having less than 2, preferably less than 1, weight percent of ammonium sulfate, less than 2 weight percent alkanolamines, e.g. ethanolamines, and less than 1 weight percent alkylene glycol, e.g. ethylene glycol, with a fatty acid containing from about 8 to about 18 carbon atoms, e.g. coco fatty acid, at temperatures of from 150° C. to 200° C.

In carrying out the preparation of ammonium alkanoyl alkyl sulfonates from an aqueous solution of ammonium hydroxyalkyl sulfonate, e.g. ammonium isethionate, of the present invention, it is common to employ at least a stoichiometric amount of the fatty acid reactant. Commonly, a molar excess of the monocarboxylic fatty acid is used, e.g. from about 3 to about 10 percent molar excess. However, an excess of the ammonium hydroxyalkyl sulfonate reactant may also be used. Thus, the mole ratio of fatty acid to ammonium hydroxyalkyl sulfonate will typically range from about 0.95:1 to about 1.1:1. Care should be observed to avoid a large excess of fatty acid since the presence of fatty acid and alkylene glycol esters, e.g. ethylene glycol esters, in the product can result in turbid aqueous solutions of the ammonium alkanoyl alkyl sulfonate, e.g. ammonium cocoyl isethionate, which are of limited use in clear cosmetic, e.g. shampoo, formulations. The amount of fatty acid impurity present in the final ammonium alkanoyl alkyl sulfonate product is commonly less than five weight percent, e.g. in the three to four weight percent range. Preferably, the amount of fatty acid impurity is less than three weight percent. The amount of alkylene glycol ester is preferably less than 2 weight percent, and more preferably less than 1 weight percent to produce clear liquid products.

Reaction temperatures for the condensation reaction of ammonium hydroxyalkyl sulfonate and fatty acid are typically in the range of from 150° to 200° C. For the condensation of isethionate isethionate and coco fatty acid, condensation temperatures typically range from about 150° to 190° C., e.g. about 180° C. At temperatures greater than 200° C., charting of the condensation product is likely to occur and, therefore, such high temperatures are to be avoided. Hence, temperatures below that at which charring of the ammonium alkanoyl alkyl sulfonate product occurs are used.

The condensation reaction is typically initiated under an inert gaseous atmosphere, e.g. a nitrogen purge, until by-product water, which results from the condensation reaction, has been removed, and the reaction mixture becomes homogeneous. Thereupon, a slight vacuum, about 500 to 700 millimeters (mm) of mercury (Hg), is applied to the reaction vessel to reduce the pressure to subatmospheric levels, and the reaction continued at the aforedescribed reaction temperatures until the reaction is essentially completed, whereupon full vacuum, about 5 to 10 mm of Hg, is applied to remove unreacted fatty acid. Thereafter, the vacuum is released, and the product removed from the reaction vessel.

The aforedescribed reaction proceeds readily in the absence of catalyst when significant levels (as described above)of alkanolamine, ammonium sulfate and alkylene glycol impurities are absent. Such reaction typically initiates within about one to two hours after attaining reaction temperature and is completed within about six to ten hours. Optionally, catalytic amounts of conventional catalyst materials may be used to enhance the condensation reaction. Such catalysts include, without limitation, dodecylbenzenesulfonic acid (DDBSA), p-toluenesulfonic acid (PTSA), zinc oxide and quaternary ammonium compounds such as stearyltrimethyl ammonium chloride, and mixtures of such catalysts. Catalytic amounts of such materials typically range from about 0.1 to about 3 weight percent, based on the weight of the reactants. The reaction mixture may further comprise a small quantity of previously formed ammonium alkanoyl alkyl sulfonate, e.g. ammonium cocoyl isethionate, referred to herein as a "heel", which may comprise up to 20 percent, preferably about 5 to 12 percent, by weight of the total solids, i.e. ammonium hydroxyalkyl sulfonate, fatty acid and heel.

The ammonium alkanoyl alkyl sulfonate, e.g. ammonium cocoyl isethionate, product prepared in accordance with the process of the present invention may be obtained in yields of at least about 90 percent, and at least about 85 percent purity. The purity of the ammonium alkanoyl alkyl sulfonate product preferably ranges from about 88 to 97 percent, e.g. about 90 to 92 percent. The major impurity in the final product is typically unreacted fatty acid which is preferably less than five weight percent, and may be in the three to four weight percent range, but is most preferably less than three percent. The anionic activity of the product is at least 85 percent, and preferably is about 88 to 97 percent, based on solid ammonium alkanoyl alkyl sulfonate. Ammonium cocoyl isethionate having an anionic activity of less than 85 percent based on solid ACI forms turbid aqueous solutions which are not useful for the preparation of clear commercial formulations used in cosmetic products, such as clear shampoos. The anionic activity of the ammonium alkanoyl alkyl sulfonate products of the present process may be measured by ASTM Test Ammonium alkanoyl alkyl sulfonates, such as ammonium cocoyl isethionate (ACI), are solids at room temperature. ACI is a stiff paste even at higher temperatures. Such products are, therefore, inherently difficult to remove from the reaction vessel in which they are prepared. While it would be convenient to remove such materials from the reaction vessel as a solution in water, materials such as ACI are unstable in aqueous solution under acidic conditions. Aqueous solutions of ammonium cocoyl isethionate generally have a pH of about 3.0 to 3.5. Due to its acid pH, ACI hydrolyzes easily when dissolved in water in the reaction vessel at elevated temperatures, thereby resulting in the loss of product.

It is disclosed in copending U.S. Ser. No. 07/721,741 that solid ammonium alkanoyl alkyl sulfonate product may be removed readily from the reaction vessel by dissolution in water without significant hydrolysis if the natural acidity of the product is adjusted to within a pH range of from about 6 to about 8, preferably about 6.5 to 7.5, e.g. 6.7 to 7.2. In adjusting the acidity of the product, it is preferred that the product first be cooled from reaction temperatures to about 120° C. or less, e.g. from about 50° to 120° C. The acidity of the ammonium alkanoyl alkyl sulfonate product may be adjusted with any suitable alkaline reagent, preferably substantially water-free, more preferably anhydrous, also preferably high boiling, e.g. relatively non-volatile at the temperature at which the product acidity is adjusted, and also preferably acceptable for use in cosmetic applications. After adjustment of the acidity, sufficient water may be mixed with the "neutral" ammonium alkanoyl alkyl sulfonate product to dissolve it and form an aqueous solution thereof.

The addition of alkaline reagent and preferably subsequent addition of sufficient water to dissolve the product are performed with vigorous agitation to avoid localized conditions of high alkalinity (or high acidity) in the reaction product and to assist in the formation of an aqueous solution that may be readily removed from the reactor. Because the cooled product is in the form of a solid or stiff paste, several hours of stirring are required to dissolve all of the solid product. The resultant aqueous solution usually will have a concentration of about 40 weight percent or less. Concentrations of from 25 to 35 weight percent are preferred to avoid gelling of the product. Because the ammonium hydroxyalkyl sulfonate, e.g. ammonium isethionate, prepared in accordance with the controlled pH method of the present invention contains low levels of alkanolamines, alkylene glycol and ammonium sulfate, the ammonium alkanoyl alkyl sulfonate produced therefrom forms clear, i.e. non-turbid, solutions at room temperature at these concentrations.

The present invention is more particularly described in the following examples, which are intended as illustrative only, since numerous modifications and variations thereof will be apparent to those skilled in the art.

EXAMPLE I

A one liter stainless steel autoclave was charged with 300 grams of ammonium bisulfite solution (57.1% assay $NH_4HSO_3$) having an initially low pH of 4.94, along with 211 grams of deionized water. The autoclave was pressure purged with nitrogen to remove air. The autoclave was heated to 35° to 40° C., and 76 grams of ethylene oxide was added in portions as needed to keep the temperature at about 35° C. with cooling water on, and the pressure less than 35 pounds per square inch gage (psig), or 3.5 kilograms per square centimeter ($kg/cm_2$). When the addition of ethylene oxide was complete, the temperature was maintained at approximately 35° C. for several hours. Samples of the reaction mixture were taken during this period and analyzed for pH and sulfite, $SO_3^=$, content with the following results.

| Hours | pH | Weight % $SO_3^=$ |
|---|---|---|
| 1.5 | 7.1 | 2.3 |
| 2.5 | 8.4 | 0.63 |
| 3.5 | 8.4 | 0.34 |

The first sample above indicated that the reaction was about 91.5 percent complete before the pH increased to above 7, as calculated from the weight percent residual sulfite. Following analysis of the last sample, vacuum was applied to the reaction mixture for 45 minutes to strip out excess ethylene oxide. The stripped reaction mixture was analyzed and found to contain, by weight, 0.13 percent $SO_3^=$, 0.29 weight percent ethylene glycol, and 47.7 percent solids. Analysis by $^{13}C$ NMR showed the presence of 0.9 mole percent ethanolamine.

Into a stirred reaction flask were placed 304 grams of the above aqueous ammonium isethionate (~1 mole), 233 grams of coco fatty acid (1.1 mole), and 88 grams of previously prepared aqueous ammonium cocoyl isethionate (31.0 weight percent solids in aqueous solution). The fatty acid used in all of the examples herein is C-108 fatty acid from the Procter & Gamble Co. The reaction mixture was heated to 110° C., and the water was removed by vacuum stripping for 45 minutes under approximately 100 mm pressure.

The reaction flask was opened, 1 gram of p-toluenesulfonic acid monohydrate catalyst was added, the flask was resealed and heated to 150° to 160° C. with a nitrogen purge. After 3.5 hours, the reaction mixture coupled to become one phase, and the temperature was maintained for one additional hour. Then excess fatty acid was removed by vacuum stripping at approximately 10 mm Hg pressure for 4 hours at the same temperature.

The vacuum was released with nitrogen, and the reaction mixture cooled to 110° C. An aqueous solution of 1.5 grams concentrated ammonium hydroxide in 800 grams of water was added, and the mixture was stirred at 50° to 60° C. until completely dissolved. The final solution had a pH of 6.1, 30.9 percent solids, with an anionic activity of 27.7 percent (89.6 percent anionic activity on solids basis). When chilled to become cloudy and subsequently warmed, the solution became clear at 15° C. (clear point).

EXAMPLE II

Commercially available ammonium bisulfite solution (60.9 percent assay $NH_4HSO_3$) was obtained from the manufacturer, P.B.& S. Chemical Company, inc. Sulfur dioxide gas was bubbled into the solution at 10° C. until the pH dropped to 4.8.

A stainless steel autoclave was charged with 800 grams of the above solution along with 232 grams of deionized water. The vapor space of the reactor was purged with nitrogen to remove air, and the autoclave was heated to 35° to 40° C. Then 220 grams of ethylene oxide (EO) was added, keeping the temperature at about 35° to 40° C. Following completion of the addition of EO, the reaction was continued for 1 hour, and the reaction mixture was sampled and found to contain 3.9 weight percent residual sulfite anion, and have a pH of 5.7. An additional 5 grams of ethylene oxide was added, and the reaction was continued for 1 hour. Analysis of a sample of reaction mixture indicated a residual sulfite anion content of 2.3 weight percent, indicating that the reaction had proceeded 94.3 percent toward completion, and a pH of 6.0, so an additional 10 grams of ethylene oxide was added, followed by an additional 1 hour reaction period. Analysis of the reaction mixture then showed that the sulfite anion content had dropped to 0.47 weight percent, and the pH had increased to 7.7. No additional ethylene oxide was added. The reaction was continued for 1 hour, and the sulfite content dropped further to 0.3 weight percent, with a pH of 7.76. After 1 final hour of reaction time, the reaction mixture was vacuum stripped to remove any residual ethylene oxide, and the final analysis indicated a residual sulfite anion content of 0.24 weight percent, a pH of 8.4, a solids content of 60.5 weight percent, and an ethylene glycol content of 0.68 weight percent. By $^{13}C$ NMR analysis, 0.4 mole percent ethanolamine was also found to be present.

Into a stirred reaction flask were placed 247 grams of the above aqueous ammonium isethionate, 223 grams of coco fatty acid, and 80 grams of previously prepared aqueous ammonium cocoyl isethionate solution (30.9 percent solids). The reaction mixture was heated to 110° C. and most of the water was stripped off. The reaction flask was opened, 1 gram of p-toluenesulfonic acid monohydrate catalyst was added, the flask was resealed and heated to 150° to 60° C. with a nitrogen purge. After 7.5 hours at the above temperature, the excess fatty acid was stripped off under vacuum for 4 additional 8 hours at 10 mm of Hg or less.

The vacuum was released with nitrogen and the reaction mixture was cooled to 110° C. An aqueous solution of 1.2 grams of concentrated ammonium hydroxide in 800 grams of water was added and the mixture was stirred until completely dissolved. The final solution had an anionic activity of 27.7 percent at a 31.0 percent. solids concentration (89.4 percent anionic activity on solids basis). When chilled to become cloudy and subsequently warmed, the solution became clear at 19° C. (clear point).

Comparative Example A

To illustrate the effect of uncontrolled high pH in the preparation of ammonium isethionate on the ammonium cocoyl isethionate prepared therefrom, commercially available ammonium bisulfite solution (57.9 percent assay $NH_4HSO_3$) was obtained from the manufacturer, P.B.& S. Chemical Company, Inc., and the pH of the solution, 5.5 as received, was not controlled in accordance with method of the invention. A one gallon stainless steel autoclave was charged with 1680 grams of the ammonium bisulfite solution and 1228 grams of deionized water. The autoclave was purged twice with nitrogen in order to remove air. The ammonium bisulfite solution was heated to 30° C., and 430 grams of ethylene oxide (EO) added in amounts as required to maintain the temperature at 30° to 35° C. and the pressure below 40 psig (3.8 kg/cm$^2$). After all the EO had been added, the reaction was continued for one hour. The reaction mixture was analyzed and found to contain a high level of residual sulfite anion. Three additions of ethylene oxide were made of 30, 30 and 60 grams. Finally, the reaction mixture was vacuum stripped to remove any unreacted ethylene oxide. The ammonium isethionate reaction product contained 0.91 weight percent sulfite anion and 0.36 weight percent ethylene glycol. Analysis by $^{13}C$ NMR indicated the presence of 14.7 mole percent ethanolamine, 4.8 mole percent diethanolamine and 0.9 mole percent triethanolamine.

The above ammonium isethionate solution contained 47.8 percent solids. A stirred reaction flask was charged with 192 grams of this ammonium isethionate solution (0.6 moles). The solution was heated to 36° C. under nitrogen, then vacuum stripped at 8 millimeters mercury for 45 minutes. To this solution were added 138 grams (10 percent molar excess) of coco fatty acid and 0.12 gram of 50 percent aqueous hypophosphorous acid (HPPA). The reaction mixture was gradually heated to 110° C. and held at that temperature until the distillation of water slowed. The reaction mixture was then vacuum stripped at about 5 millimeters of mercury for 2 hours. An additional 0.2 gram of HPFA was added, and the temperature was slowly increased to 175° C. The reaction mixture was held at 175° C. for 6.4 hours then cooled to about 150° to 160° C. An additional 0.19 gram of HPPA was added, and the reaction mixture was vacuum stripped at about 6 millimeters of mercury for 4 hours. After cooling to about 30° C. under nitrogen the very hard solid product was broken up with a spatula and dissolved in 410 grams of water containing 1.2 grams of triethanolamine (TEA), maintaining the temperature of the solution at about 50° to 60° C. and the pH at 7±0.5 by addition of TEA as needed. An additional 3.34 grams of TEA was needed.

The final solution of ammonium cocoyl isethionate had a pH of 7.2, contained 31.4 percent solids, and had an anionic activity of 19.0 percent (60.5 percent anionic activity on solids basis). The solution was thick and cloudy at ambient temperature, and did not become clear upon warming until it reached 38° C. (clear point), which is an unacceptably high clear point for use in clear liquid compositions.

Comparative Example B

This comparative example illustrates the effect of high sulfate content in ammonium bisulfite and the ammonium isethionate produced therefrom on the ammonium cocoyl isethionate produced from such ammonium isethionate. A 70 percent aqueous solution of typical commercially available ammonium bisulfite (566.0 grams) was diluted with 225 milliliters (ml) of water and charged to a one liter autoclave. The autoclave was sealed under a positive nitrogen pressure of 10 psig (0.7 kg/cm$^2$), and the solution heated to 60° C. Ethylene oxide (EO) was added to the solution in the autoclave at a rate of about 2 grams per minute. The addition of ethylene oxide was stopped after 180 grams had been added to the autoclave. The pressure within the autoclave during most of the EO addition was 30 to 35 psig (3.1 to 3.5 kg/cm$^2$). The resultant reactant mixture was stirred at 60° C. for 1.5 hours and then cooled to 40° C. The pressure within the autoclave was released and the contents weighed. The weight gain was 175 grams and the pH of the solution was 8.4. The solution had a solids content of 60 percent and a sulfate content of 4.7 percent, which corresponded to 6.5 weight percent ammonium sulfate,.

An aqueous solution of ammonium isethionate (206 grams) prepared as above containing about 6.5 weight percent ammonium sulfate was charged to a reaction vessel equipped with mechanical stirrer, temperature controller and nitrogen inlet. The solution was heated under nitrogen to 140° C. to remove water. When the distillation of water stopped, the reactor was evacuated gradually to a subatmospheric pressure of 10 mm of mercury to remove volatiles. The vacuum was released and 209 grams of coco fatty acids (DDBSA) catalyst were added to the residue dodecylbenzenesulfonic acid (DDBSA) catalyst were added to the residue in the reaction vessel. The reaction mixture was heated to 180° C. and stirred for 3.25 hours under nitrogen. No reaction occurred during this period. The heat to the reaction vessel was turned off and the reaction mixture allowed to stand at room temperature overnight (about 16 hours).

The reaction mixture was then reheated to 180° C. and stirred under nitrogen for 2 hours. No reaction was observed. P-toluenesulfonic acid (PTSA) catalyst (0.2 grams) was then added to the reaction mixture, and the mixture stirred for 2 hours at 180° C. No reaction was observed to occur as evidenced by the absence of a water distillate. Stearyl trimethyl ammonium chloride (0.1 grams) was then added to the reaction mixture, and the mixture heated for 1 hour at 180° C. Significant reaction was still not observed. The reaction vessel was gradually evacuated to a pressure of 10 mm of mercury and maintained at 180° C. The reaction mixture became homogeneous and thick after 4 hours under vacuum at 180° C. The vacuum on the reactor was then released and the product removed. The total reaction time at 180° C. was 14 hours. The anionic activity of the solid product was found to be 82.3 percent. The product was dark in color, and when a 30 percent aqueous solution was prepared from the product, a turbid solution was formed.

Comparative Example C

This comparative example illustrates the effect of ethylene glycol in the ammonium isethionate on the ammonium cocoyl isethionate produced therefrom. A 500 milliliter, 3-necked flask was charged with 120 grams of an aqueous ammonium isethionate solution (60 percent solids), which contained 0.8 weight percent of ammonium sulfate and about 3.7 weight percent of ethylene glycol, and 109.5 grams of C-108 coco fatty acid. The mixture was heated with stirring under a nitrogen sparge to 170° C. over a period of 1.75 hours. Most of the water contained in the reaction mixture was distilled during this time. The reaction mixture was maintained at 170° C. for 7 hours before water from the condensation reaction began to distill. The reaction mixture was maintained at 170° C. for an additional 3 hours. During this period, 50 milliliters of water and 12 milliliters of fatty acid were collected as distillates. Heat to the reactor was turned off, and the mixture allowed to stand overnight at room temperature. Distilled fatty acid was returned to the reactor and the mixture reheated with stirring to 170° C. and maintained at such temperature for 2 hours. The reaction mixture was then slowly evacuated to a pressure of 4 to 5 millimeters of mercury and maintained at such pressure for 2 hours at 170° C. The mixture was then cooled and the reaction product removed. Anionic activity of the product was found to 80.2 percent. A 30 percent aqueous solution of the product was prepared. The solution appeared turbid.

Comparative Examples

These comparative examples demonstrate what levels of ethylene glycol and ethanolamine impurities (added to crystalline ammonium isethionate, which contains insignificant amounts of these produce ACI with an unacceptably high clear point in solution.

A reaction flask was charged with 71.6 grams (0.5 moles) of crystalline ammonium isethionate, 114.8 grams (0.55 moles, 10% excess over stoichiometric) of coco fatty acid, 0.5 grams of p-toluenesulfonic acid monohydrate, and the impurity to be tested.

The nitrogen flow was started, with stirring, and the reaction mixture was heated to 150° to 160° C. and held at that temperature. After a period of time (ranging from 1 hour 10 minutes to 9 hours 25 minutes, depending on the impurity and the amount added), the two phases of the reaction mixture "coupled", i.e. became a homogeneous single phase.

The reaction mixture was maintained at 150° to 160° C. for an additional 2 to 4 hours as the viscosity increased and the reaction mixture developed a "dough-like" consistency. Excess unreacted fatty acid was removed by vacuum stripping the reaction mixture for 2.5 to 4 hours at 4 to 8 mm of Hg pressure and 150° to 160° C. After cooling, the reaction mixture was broken into small pieces, sampled for anionic activity analysis, and dissolved in water.

The solidified reaction mixture was stirred with deionized water at 50° to 60° C. The pH was monitored with a pH electrode and the pH was kept at about pH 7 (±0.5) by dropwise addition of triethanolamine as needed. Once the solids were completely dissolved, a final adjustment in concentration was made, if needed, by addition of water.

The clear point was measured by chilling the sample until it became cloudy, then allowing the sample to warm slowly. The clear point was measured as the temperature at which the sample becsne clear, or essentially clear (with just a very slight haze which did not disappear on further warming). These data in the following table show that as the level of glycol in the ammonium isethionate approaches 0.9 percent, and the level of alkanolamine 2 percent, the clear point of the ammonium cocoyl isethionate (ACI) produced therefrom approaches ambient temperature. Therefore, to provide an ammonium alkanoyl alkyl sulfonate which is clear at ambient temperature, the ammonium hydroxyalkyl sulfonate is substantially pure, i.e. has levels of these impurities below these amounts.

TABLE

| IMPURITY (Weight % of AIS) | | ACI SOLUTION | | | |
|---|---|---|---|---|---|
| Ethylene Glycol | Ethanolamine | pH | Clear Point (°C.) | % Solids | % Anionic Activity |
| 0.07 | — | 6.87 | 12 (avg.) | 31.1 | 27.3 |
| 0.07 | — | 6.95 | | 30.9 | 27.9 |

TABLE-continued

| IMPURITY (Weight % of AIS) | | ACI SOLUTION | | | |
|---|---|---|---|---|---|
| Ethylene Glycol | Ethanolamine | pH | Clear Point (°C.) | % Solids | % Anionic Activity |
| 0.73 | — | 6.93 |  15 (avg.) | 31.3 | 28.5 |
| 0.73 | — | 6.88 | | 31.2 | 27.7 |
| 0.82 | — | 7.39 | 18 | 30.3 | 26.8 |
| 0.92 | — | 7.00 | >50 | 31.4 | 28.5 |
| 0.07 | 0.82 | 7.30 | 14 | 31.4 | 27.1 |
| 0.07 | 1.21 | 6.97 | 18 | 30.5 | 26.8 |
| 0.07 | 2.02 | 7.12 | 22 | 31.4 | 26.6 |
| 0.73 | 0.82 | 7.05 | 19 | 30.6 | 26.0 |

The preceding examples are offered to illustrate the present invention. Various modifications of the invention are included within the scope as defined by the following claims.

We claim:

1. A method for producing ammonium alkanoyloxy alkyl sulfonate of the general formula,

RCO(O)R'SO₃M wherein R is a monovalent hydrocarbon residue of a fatty acid containing from 6 to 24 carbon atoms, R' is a bivalent hydrocarbon radical containing from 2 to 4 carbon atoms, and M is the ammonium cation, comprising:

(a) reacting an aqueous solution of ammonium bisulfite with an alkylene oxide containing from 2 to 4 carbon atoms while maintaining the solids concentration of the reaction mixture at less than 70 weight percent and the pH of the reaction mixture in the range of 4.3 to 7 until the reaction is at least 90 percent complete, as measured by the amount of residual sulfite in the reaction mixture, thereby to produce a product consisting essentially of ammonium hydroxyalkyl sulfonate of the general formula,

HOR'SO₃M wherein R' and M are as defined above, said product containing alkylene glycol by-product;

(b) stripping ammonium hydroxyalkyl sulfonate prepared in a) to remove alkylene glycol, and (c) reacting ammonium hydroxyalkyl sulfonate having not more than 1 weight percent alkylene glycol, not more than 2 weight percent alkanolamine, and not more than about 2 weight percent ammonium sulfate, all based on the weight of the ammonium hydroxyalkyl sulfonate, with a fatty acid containing from 6 to 24 carbon atoms at temperatures in the range of from 150° to 200° C., thereby to produce an ammonium alkanoyloxy alkyl sulfonate of the above general formula, a 30 weight percent aqueous solution of which is non-turbid at room temperature.

2. The method of claim 11 wherein the bivalent hydrocarbon radical, R', is the ethylene bivalent radical, and the alkylene oxide is ethylene oxide.

3. The method of claim 2 wherein the fatty acid contains from 8 to 18 carbon atoms.

4. The method of claim 1 wherein the initial pH of the ammonium bisulfite solution prior to reaction with alkylene oxide is in the range of 4.5 to 5.2.

5. The method of claim 4 wherein the pH is in the range of 4.6 to 5.0

6. The method of claim 1 wherein the pH of the reaction mixture in part (a) is maintained within the range of 5.5 to 7.0 substantially throughout the reaction by the addition of an acidic neutralizing agent.

7. The method of claim 6 wherein the acidic neutralizing agent is sulfurous acid or SO₂.

8. The method of claim 3 wherein the ammonium hydroxy alkyl sulfonate used in part (c) contains not more than 0.85 weight percent alkylene glycol.

9. The method of claim 2 wherein the ammonium alkanoyloxy alkyl sulfonate has an anionic activity of greater than 85 percent.

10. The method of claim 3 wherein the ammonium alkanoyloxy alkyl sulfonate has an anionic activity of greater than 85 percent.

11. The method of claim 3 wherein the pH of the reaction mixture is maintained below about 7 during the reaction of part (a) by (i) establishing the initial pH of the ammonium bisulfite reaction mixture in the range of 4.5 to 5.2, or (ii) adding an acidic neutralizing agent to the reaction mixture as required to maintain the pH within the range of 5.5 to 7.

12. The method of claim 11 wherein the fatty acid is coco fatty acid.

13. The method of claim 12 wherein the ammonium alkanoyloxy alkyl sulfonate has an anionic activity of greater than 85 percent, and wherein a 30 weight percent aqueous solution of said ammonium alkanoyloxy alkyl sulfonate is non-turbid at 22° C.

14. The method of claim 13 wherein the ammonium hydroxyalkyl sulfonate used in part (c) contains less than about 0.9 weight percent alkylene glycol.

15. The method of claim 14 wherein the ammonium hydroxy alkyl sulfonate used in part (c) contains less than about 1 weight percent ammonium sulfate.

16. Ammonium alkanoyloxy alkyl sulfonate prepared by the method of claim 1.

17. Ammonium alkanoyloxy alkyl sulfonate prepared by the method of claim 3.

18. Ammonium cocoyl isethionate prepared by the method of claim 14.

19. A clear liquid detergent composition comprising an aqueous solution of the ammonium alkanoyloxy sulfonate of claim 15.

20. A clear liquid shampoo composition comprising an aqueous solution of the ammonium cocoyl isethionate of claim 18.

* * * * *